United States Patent
DeNoble

(12) 
(10) Patent No.: US 11,490,928 B2
(45) Date of Patent: Nov. 8, 2022

(54) GYNECOLOGICAL DEVICE, SYSTEM AND METHOD OF USING

(71) Applicant: Shaghayegh DeNoble, Wayne, NJ (US)

(72) Inventor: Shaghayegh DeNoble, Wayne, NJ (US)

(*) Notice: Subject to any disclaimer, the term of this patent is extended or adjusted under 35 U.S.C. 154(b) by 50 days.

(21) Appl. No.: 17/205,409

(22) Filed: Mar. 18, 2021

(65) Prior Publication Data

US 2022/0296462 A1    Sep. 22, 2022

(51) Int. Cl.
| A61B 17/42 | (2006.01) |
| A61F 13/00 | (2006.01) |
| A61F 13/14 | (2006.01) |
| A61H 19/00 | (2006.01) |

(52) U.S. Cl.
CPC ........ *A61B 17/42* (2013.01); *A61F 13/00085* (2013.01); *A61F 13/148* (2013.01); *A61H 19/50* (2013.01); *A61H 19/30* (2013.01); *A61H 2201/169* (2013.01)

(58) Field of Classification Search
CPC ............ A61F 13/148; A61F 2007/0048; A61F 2007/005; A61F 5/03; A61H 19/50; A61H 19/30; A61H 2201/169
See application file for complete search history.

(56) References Cited

U.S. PATENT DOCUMENTS

| 2009/0148503 A1* | 6/2009 | Trieu ..................... A61B 17/42 424/447 |
| 2011/0022056 A1* | 1/2011 | Haadem ................ A61F 5/0093 606/119 |
| 2013/0334084 A1* | 12/2013 | Arbesman ............... A61F 17/00 206/441 |
| 2014/0213956 A1* | 7/2014 | Arbesman ............. A61F 13/061 602/60 |
| 2015/0313636 A1* | 11/2015 | Shen ..................... A61F 5/0093 606/119 |
| 2016/0262943 A1* | 9/2016 | Arbesman ......... A61F 13/00059 |
| 2017/0049602 A1* | 2/2017 | Kuehl ................. A61F 13/0273 |

FOREIGN PATENT DOCUMENTS

| WO | WO-2018130917 A1 * | 7/2018 | ............ A61B 17/42 |
| WO | WO-2019195097 A1 * | 10/2019 | ............ A61B 17/42 |

* cited by examiner

*Primary Examiner* — Kaylee R Wilson

(74) *Attorney, Agent, or Firm* — Wendi E. Uzar

(57) ABSTRACT

A gynecological device that corrects a vaginal opening that is large or stretched out without requiring surgery. The stretchable gynecological device includes a main body having a front surface, a rear surface, a first end, a second end, a first edge, a second edge, and an adhesive on the rear surface of the main body. The gynecological device also includes at least two arms having a front surface, a rear surface, a first end, a second end, a first edge and a second edge that extend outwardly from the second edge of the main body. An adhesive is on the rear surface of the arms. To apply the gynecological device, the arms are firmly pressed down to the vaginal vestibule bilaterally, the main body is then pulled up above the clitoral hood and then applied and pressed down across the lower abdomen towards the anterior superior iliac spines.

10 Claims, 5 Drawing Sheets

GYNECOLOGICAL DEVICE, SYSTEM AND METHOD OF USING

FIELD OF THE INVENTION

The invention relates to a gynecological device to be applied to the vaginal area to increase friction during sexual intercourse and provide greater sexual satisfaction. In particular, an improved device that can be easily applied before sexual intercourse to achieve a non-surgical perineoplasty. The device narrows the vaginal opening, or introitus, that is large in diameter or stretched out from aging or after childbirth. The device may also aid in the retracting the clitorial hood to expose the clitoris during intercourse.

BACKGROUND OF THE INVENTION

Many women experience widening of the vagina and perineum and looseness of the area between the vaginal opening and anus after vaginal childbirth. This can cause a gaping of the vaginal opening which leads to reduced friction during sexual intercourse and diminished sexual satisfaction for the woman and her partner. The main option to treat this problem has been a surgical perineoplasty, or perineorrhaphy procedure which is a surgical procedure where redundant tissue is excised from the distal vagina and the introitus is tightened by reapproximating the superficial transverse perineal and bulbocavernosus muscles. Complications of surgery include infection, fistula formation, and over-narrowing causing stenosis and pain with intercourse. A separate issue some women experience is enlarged clitoral hood that can make clitoral stimulation difficult during intercourse.

Therefore, there is a need for a non-surgical product that is easy to apply and can narrow the vaginal opening to produce increased friction during sexual intercourse and retract the clitoral hood to increase clitoral stimulation.

SUMMARY OF THE INVENTION

The present invention seeks to solve the challenge of narrowing the vaginal opening that is large in diameter or stretched out after childbirth during sexual intercourse by providing a device that eliminates the need for surgery, which achieves the purpose set forth above as follows:

The gynecological device for tightening the vaginal opening during sexual intercourse comprises a main body having a front surface, a rear surface, a first end, a second end, a first edge, a second edge, and a central area between said first and second end, an adhesive on the rear surface of the main body, a plurality of arms having a front surface, a rear surface, a first end, a second end, a first edge and a second edge that extend from said central area of said second edge of the main body, an adhesive on the rear surface of the arms, wherein the length of the main body from the first end to the second end is longer than the length of the arms, from the first end to the second end.

The gynecological device may be made from a stretchable material such as high stretch adhesive support tape, medical grade tape, or elastic which can be made from 100% cotton, polyester and cotton blend, or polyurethane, rayon or synthetic fibers. A polyester and cotton blend is preferred. It is preferred that the gynecological device be a single use item. It is contemplated that it may be used for multiple uses.

The adhesive may cover the entire second surface of the main body and the arms or a portion of the second surface of the main body and the arms which provides a way for the device to adhere to skin of the user. If the gynecological device is made from high stretch adhesive support tape or medical grade tape the adhesive will uniformly cover the rear surface. It is contemplated that the adhesive may consist of any product known to those skilled in the art including, but not limited to, medical grade tape, acrylic adhesive, silicone adhesive and hydrocolloid adhesive.

Preferably the main body has a generally rectangular shape but it may be circular, triangular, or any other shape or polygon. Alternatively, the main body may have curved edges, or an edge that is convex or concave. The length of the main body from the first end to the second end is sized to extend the length of a user's lower abdomen. The width of the main body from the first edge to the second edge may vary and is sized and shaped to secure the device to the user in the correct position.

Preferably there are two arms. In the preferred embodiment, the arms have an convex first edge and a parallel second edge where the first arm and the second arm are mirror images of one another. Alternatively, the arms may be generally rectangular, oval, circular, have concave edges or have any other shape. The arms may extend from the main body adjacent to one another. Alternatively, the arms may extend from the main body spaced apart from one another. It is contemplated that additional arms be added to the gynecological device. The arms may be the same length or different lengths. Preferably the arms are the same length from the first end to the second end and are sized to extend the length of a user's vagina vestibule.

To use the method of the present invention, each arm is applied to the vagina vestibule bilaterally by pressing the adhesive of the rear surface of each arm down firmly. Once the arms are secured, the main body is pulled upward toward the user's abdomen so that the main body is positioned above the clitoral hood of the user. The first end and second end of the main body are applied bilaterally to the lateral mons across the lower abdomen towards the anterior superior iliac spines by pressing the adhesive of the rear surface of the main body down firmly. This acts to pull the arms of the gynecological device and vagina vestibule upward and thereby tighten the vaginal opening, lift the clitoral hood and expose the clitoris.

The method of tightening the vaginal opening comprises providing a user having a vagina vestibule, a clitoral hood and a lower abdomen, providing a gynecological device having a main body with a front surface, a rear surface, a first end and a second end, providing an adhesive on the rear surface of the main body, providing a plurality of arms having a front surface, a rear surface, a first end and a second end, that extend generally perpendicular from the approximate center of the first end and the second end of the main body, providing an adhesive on the rear surface of the arms, wherein the length of the main body from the first end to the second end is longer than the length of the arms, from the first end to the second end, providing the gynecological device made from a stretchable material, applying the arm to the vagina vestibule bilaterally by pressing the adhesive of the rear surface of each arm down firmly, pulling the main body upward so that the main body is positioned above the clitoral hood, and applying the first end and the second end of the main body bilaterally to the lateral mons across the lower abdomen towards the anterior superior iliac spines by pressing the adhesive of the rear surface of the main body down firmly.

A gynecological tightening system, comprising a gynecological device for tightening the vaginal opening during sexual intercourse comprising: a main body having a front surface, a rear surface, a first end and a second end, an adhesive on the rear surface of the main body, a plurality of arms having a front surface, a rear surface, a first end and a second end, that extend generally perpendicular from the approximate center of the first end and the second end of the main body, an adhesive on the rear surface of the arms, wherein the length of said main body from the first end to the second end is longer than the length of the arms, from the first end to the second end, and wherein the gynecological tightening device is made from a stretchable material for: applying each arm to the vagina vestibule bilaterally by pressing the adhesive of the rear surface of each arm down firmly, pulling the main body upward so that the main body is above the clitoral hood, applying the first end and the second end of the main body bilaterally to the lateral mons across the lower abdomen towards the anterior superior iliac spines by pressing the adhesive of the rear surface of the main body down firmly.

BRIEF DESCRIPTION OF THE DRAWINGS

A preferred embodiment of the present invention has been chosen for purposes of illustration and description and is shown in the accompanying drawings forming a part of the specification wherein.

DETAILED DESCRIPTION OF THE PREFERRED EMBODIMENTS

Figure 1:
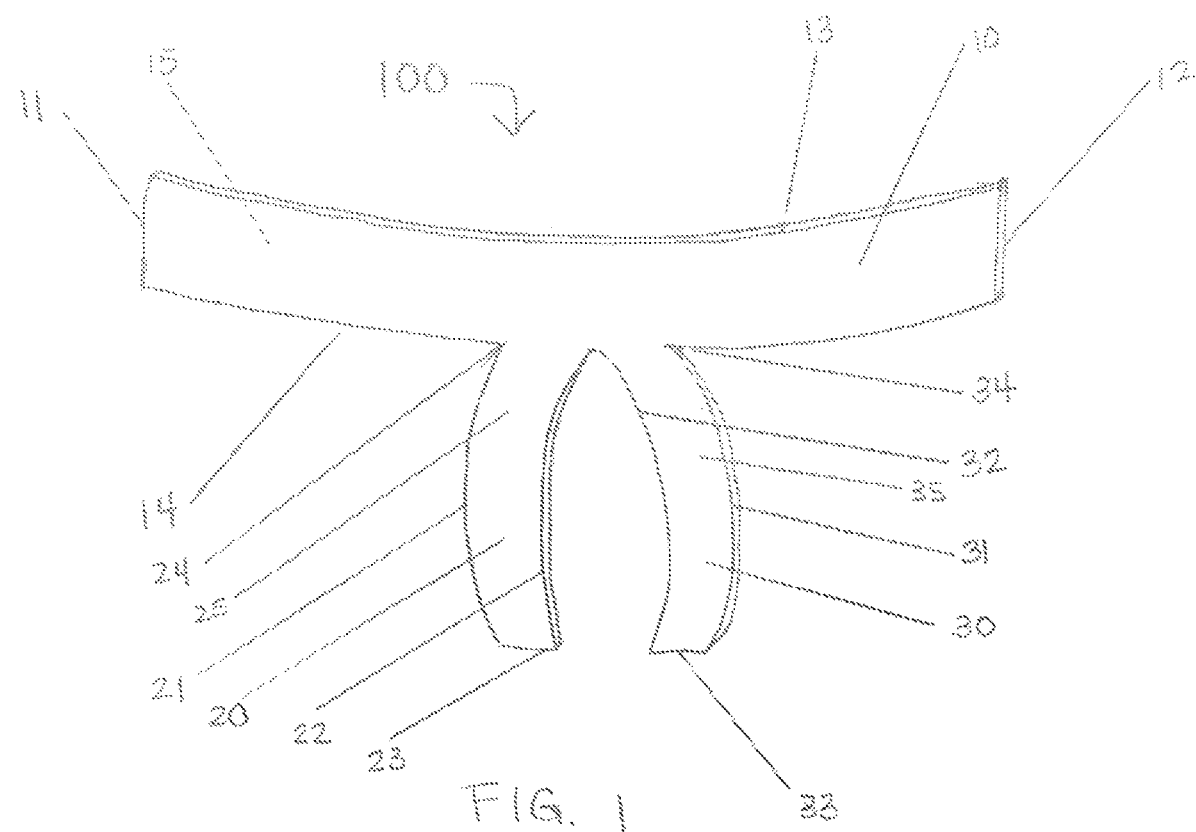
FIG. 1 is a perspective view of the gynecological device of the present invention.

With reference to the drawings, wherein the same reference number indicates the same element throughout, there is shown in FIG. 1 a perspective view of a gynecological device 100 of the present invention. As shown in FIG. 1, the gynecological device 100 includes a main body 10 having a front surface 15, a rear surface (not shown), a first end 11, a second end 12, a first edge 13, a second edge 14, and a central area between said first and second end 11, 12 and an adhesive is on the rear surface (not shown) of the main body 10. The gynecological device 100 also includes a plurality of arms 20, 30 having a front surface 25, 35, a rear surface (not shown), a first end 23, 33, a second end 24, 34, a first edge 21, 31 and a second edge 22, 32 that extend outwardly from the central area of the second edge 12 of the main body 10. An adhesive (not shown) is on the rear surface of the arms 20, 30. The length of the main body 10 from the first end 11 to the second end 12 may be longer than the length of the arms 20, 30, from the first end 23, 33 to the second end, 24, 34. It is contemplated that the length of the arms 20, 30 be the same length as the length of the main body 10. The gynecological device 100 is made from a stretchable material such as elastic.

As shown in FIG. 1 the main body 10 may be generally rectangular. It is contemplated that the main body 10 can be circular, triangular, or any other shape or polygon. Alternatively, the main body 10 may have a curved first edge 13 or second edge 14 such as convex or concave. The length of the main body 10 from the first end 11 to the second end 12 is sized to extend the length of a user's lower abdomen and therefore may be offered in different sizes to accommodate different sized users. The width of the main body 10 from the first edge 13 to the second edge 14 may vary based on the size of the user however it is sized to secure the device to the user in the correct position.

As shown in FIG. 1 the arms 20, 30 may be generally rectangular however in the preferred embodiment of the invention, the arms 20, 30 have an convex first edge 21, 31 and a second edge 22, 32 that is parallel to the first edge 21, 31. In the preferred embodiment the first arm 20 is a mirror image of the second arm 30. It is contemplated that the arms 20, 30 may be generally rectangular, oval, circular, have concave edges, convex edges or be any other shape. It is preferable that the first end second edges of the first and second arms 21, 22, 31, 32 mirror the shape of the respective edge of the vagina vestibule A to result in a better fit and result. Preferably the arms 20, 30 are the same length from the first end 23, 33 to the second end 24, 34 and are sized to extend the length of a user's vagina vestibule. It is contemplated that the arms 20, 30 be longer or shorter.

Figure 2:
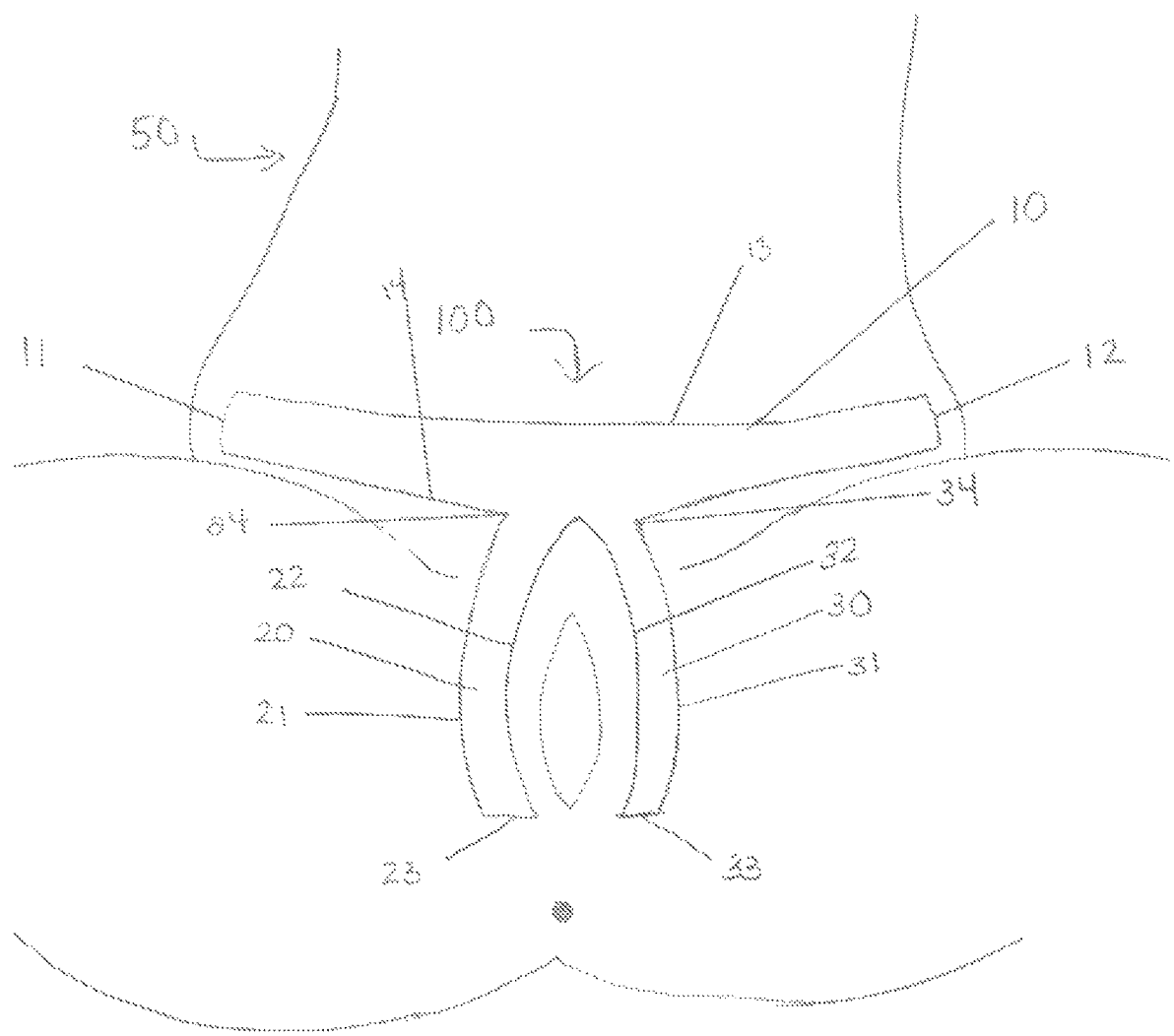
FIG. 2 is a top plan view of the gynecological device of the present invention applied on a human body part.
Figure 3:
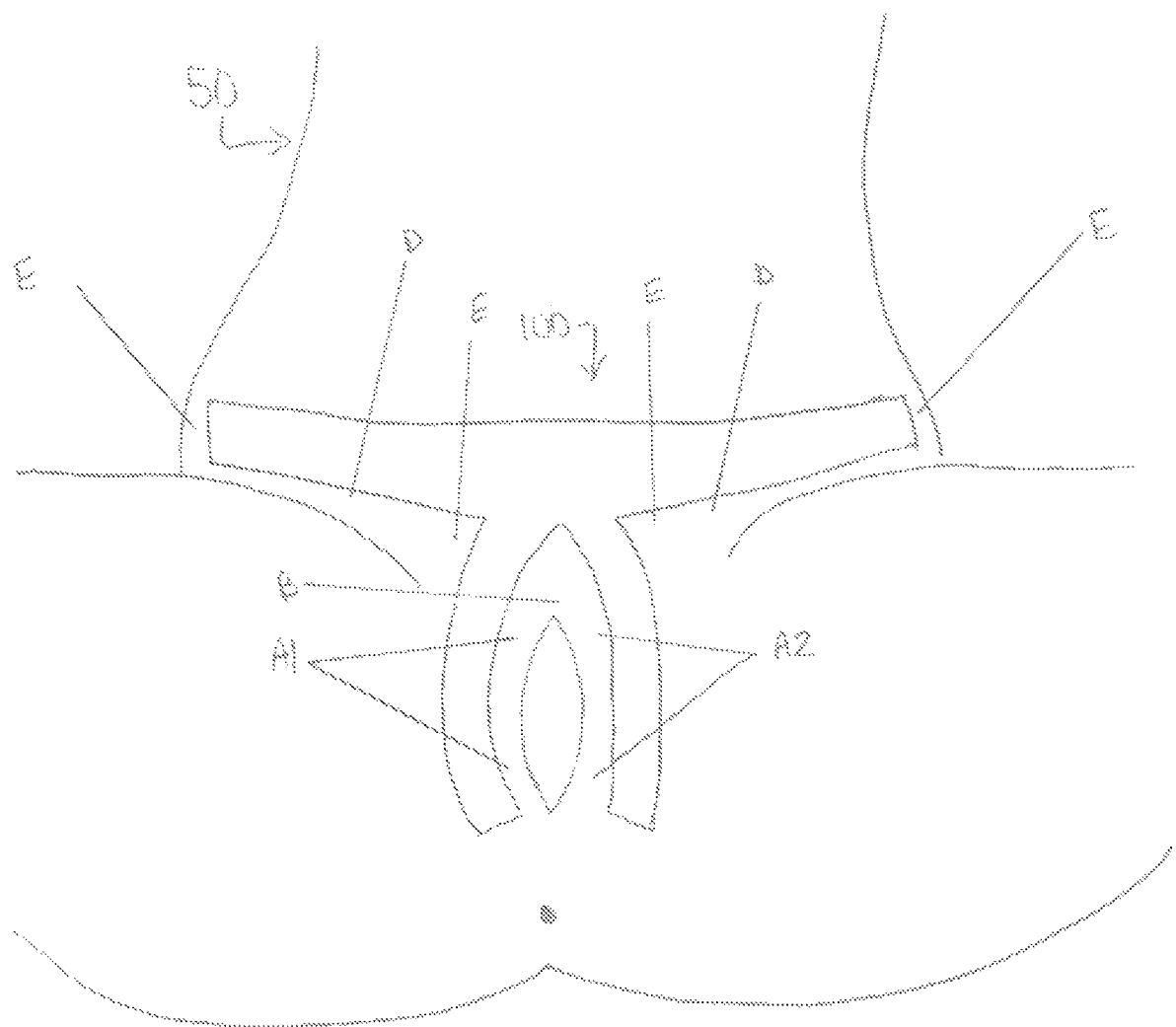
FIG. 3 is FIG. 2 showing a top plan view of the gynecological device of the present invention applied on a human body part displaying anatomy of the human body part.

As shown in FIGS. 1-3, it is preferable that the first and second arms 20, 30 extend from the main body 10 adjacent to one another.

It is contemplated that additional arms be added to the gynecological device 100. In one embodiment of the present invention, an additional arm or pair of arms may extend generally perpendicular from the first edge 13 of the main body 10. It is contemplated that the invention has four arms. The arms may be the same length or different lengths as the first 20 and second arms 30.

The rear surfaces (not shown) of the main body 10, the first arm 20 and second arm 30 are covered by an adhesive. The adhesive may consist of any product that allows the rear surface of the main body 10 and the first arm 20 and second arm 30 to be capable of adhering to human skin. The adhesive may consist of any product known to those skilled in the art including, but not limited to, medical grade tape, acrylic adhesive, silicone adhesive and hydrocolloid adhesive. The adhesive may cover the entire rear surface of the main body 10, first arm 20 and second arm 30. It is contemplated that the gynecological device 100 be made from high stretch adhesive support tape or medical grade tape resulting in the entire rear surface being adhesive. In an alternate embodiment, the adhesive may only cover a section or sections of the rear surface of the main body 10 or the arms 20, 30 such as a section close to the first edge 13, 21, 31 or the section proximate to the second edge 14, 22, 32, or the sections proximate to the first end 11, 23, 33 and the second end 12, 24, 34.

It is anticipated a film may be added to removably cover the adhesive on the rear surfaces of the main body 10 and the arms 20, 30. The film is preferably sized to mate and cover the rear surface of the main body 10 and the arms 20, 30 and thereby cover the adhesive before it is applied to the body. The film may be peeled off or removed from the rear surface of the main body 10, and arms 20, 30 to expose the adhesive on the rear surface of the main body 10 and the arms 20, 30.

Figure 4:
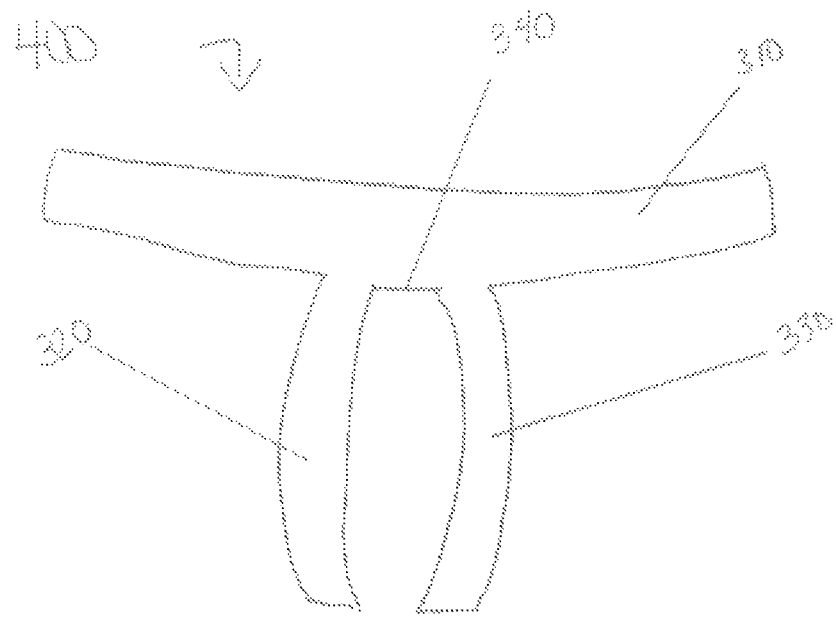
FIG. 4 is a top plan view of a second embodiment of the gynecological device of the present invention.
Figure 5:
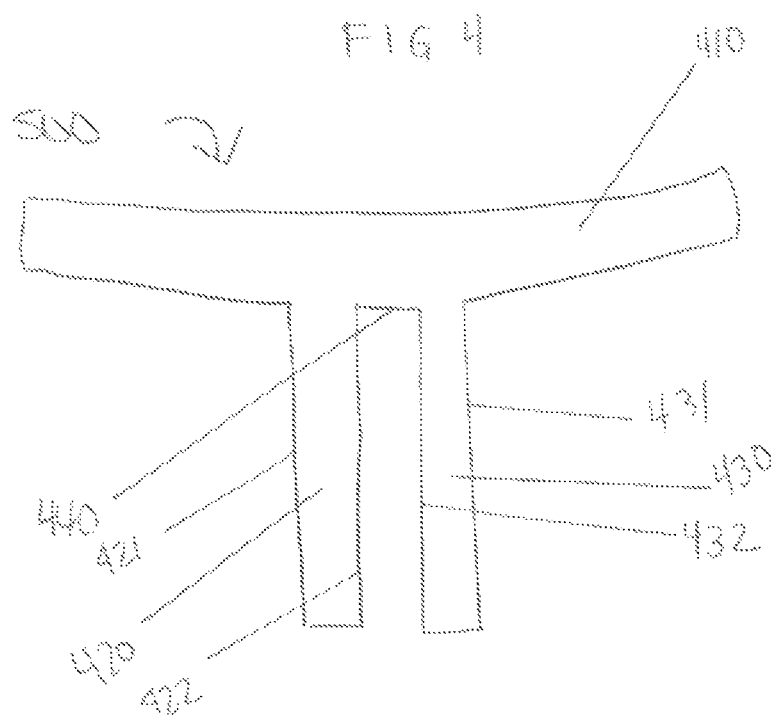
FIG. 5 is a top plan view of a third embodiment of the gynecological device of the present invention.

Alternative embodiments of the present invention are shown in FIGS. 4—7. As shown in FIGS. 4-5 for the gynecological device of the second and third embodiments of the present invention 400, 500 have first and second arms 320, 330, 420, 430 that extend from the main body 310, 410 spaced apart from one another creating a spacer or bridge 340, 440 between the first and second arms 320, 330, 420, 430. The bridge 340, 440 provides distance between the gynecological device of the second and third embodiments of the present invention 400, 500 and the clitoral hood B of the user during application. The bridge 340, 440 also allows the gynecological device 400, 500 to distribute the tension more effectively.

Figure 7:
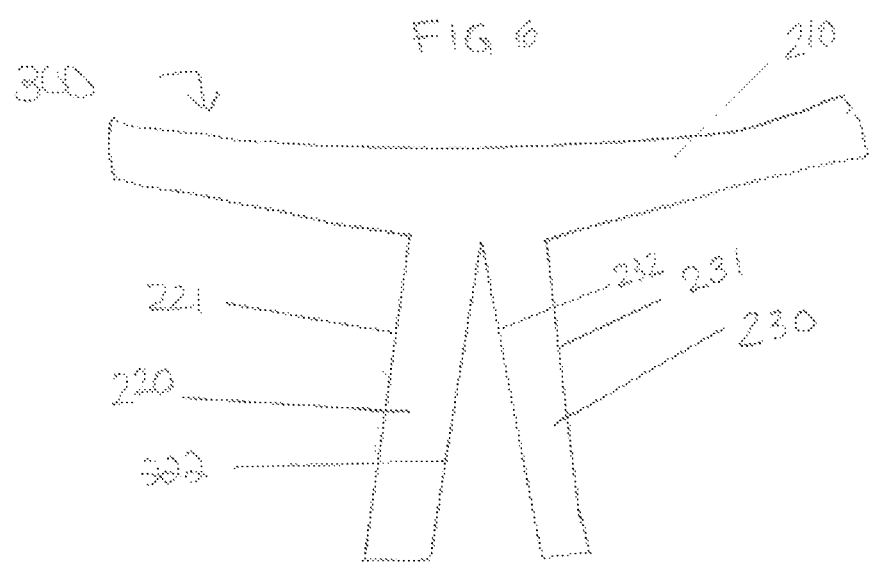
FIG. 7 is a top plan view of a fifth embodiment of the gynecological device of the present invention.

As shown in FIGS. 5 and 7 in the third and fifth embodiment of the gynecological devices of the present invention 500, 300 have arms 420, 430, 220, 230 that are generally shaped as rectangles having straight first and second edges 221, 222, 232, 231, 421, 244, 432, 431.

Figure 6:
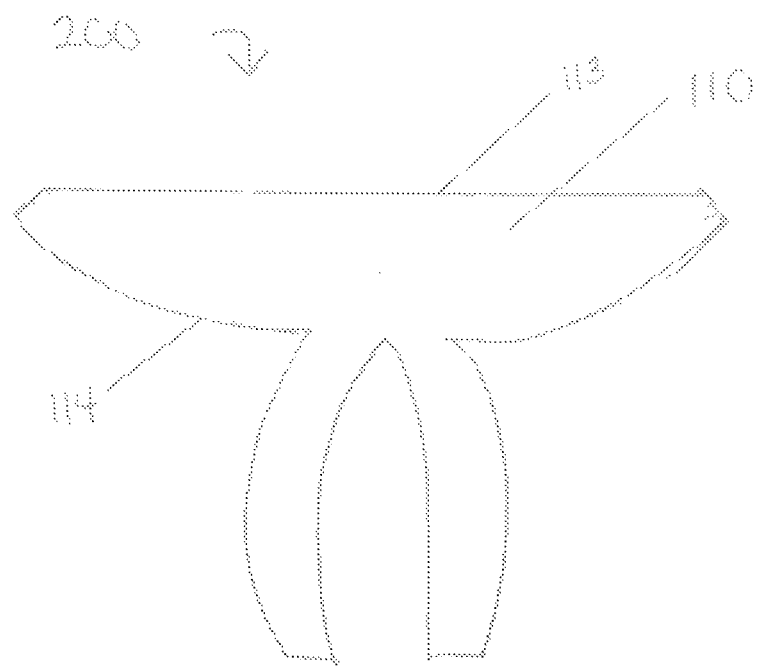
FIG. 6 is a top plan view of a fourth embodiment of the gynecological device of the present invention.

As shown in FIG. 6 in the fourth embodiment of the present invention the gynecological device 200 has a main body 110 that is generally shaped as a crescent having a rounded convex second edge 114 and a flat first edge 113.

As shown in FIGS. 2 and 3, the method of tightening the vaginal opening comprises the steps of providing a human user 50 having a vagina vestibule A1, A2, a clitoral hood B, lateral mons C, superior iliac spines E and a lower abdomen D. The gynecological device 100 as described herein is provided. Each arm 20, 30 of the gynecological device 100 is applied to the vagina vestibule A1, A2 bilaterally by pressing the adhesive of the rear surface of each arm 20, 30 down firmly. This can be accomplished by pressing down the front surface 25, 35 of each arm against each side of the vagina vestibule A1, A2 thereby applying the adhesive to the users skin. It is preferable that first arm 20 be applied to one side of the vagina vestibule A1, and then the second arm 30 be applied to the second side of the vagina vestibule A2. Once the arms 20, 30 are adhered to the vagina vestibule A1, A2, the main body 20 is pulled upward so that when the gynecological device 100 is installed the main body 20 is positioned above the clitoral hood B of the user 50. Once in position, the first end 11 and second end 12 of the main body 10 is applied bilaterally to the lateral mons C across the lower abdomen D towards the anterior superior iliac spines E by pressing the adhesive of the rear surface of the main body 10 down firmly. It is preferable that first end 11 of the main body 10 be applied to one side proximate to the anterior superior iliac spine E, and then the second end 12 of the main body 10 be applied to the proximate to the anterior superior iliac spine E. This can be accomplished by pressing down the front surface 15 of each side of the main body 10 against each side of the anterior superior iliac spine E thereby applying the adhesive to the users skin and securing the gynecological device 100 in place.

An applicator tool (not shown) having a flat edge or blade, such as a squeegee, may be used to flatten and adhere the gynecological device 100 to the user 50. Alternatively, an applicator tool such as a roller may be used.

It is contemplated that the gynecological device 100 is re-usable, the device 100 can be removed from the human user's skin and then re-applied at another time.

It is contemplated that an applicator tool (not shown) may be used to apply and pry off the gynecological device 100 so that it can be applied again.

The gynecological device and the method of applying it corrects a vaginal opening, or introitus, that is large in diameter or stretched out from aging or after childbirth without requiring surgery. After the gynecological device is applied, the vaginal opening of the user will be narrower. Benefits are increased friction with sexual intercourse, more feeling during intercourse, greater sexual gratification for the woman and her partner, and increased sexual self-confidence. The gynecological device may also help a user that is awaiting surgical repair, or would like to see how surgery may repair their vaginal opening. The gynecological device also aids in retracting the clitoral hood superiorly to help expose the clitoris during intercourse and increase pleasure.

The gynecological device 100 as displayed and described herein is applied to the human vagina vestibule, it will is contemplated that the gynecological device 100 is equally capable of supporting or aiding other body parts, either in the configuration shown or in a similar configurations having similar general features of a main body and extending arms.

As shown in FIGS. 2 and 3 and described above, the gynecological tightening system, comprises the gynecological device 100, applying each arm 20, 30 to the vagina vestibule A1, A2 bilaterally by pressing the adhesive of the rear surface of each arm 20, 30 down firmly, pulling the main body 10 upward so that the main body 10 is above the clitoral hood B, applying the first end 11 and the second end 12 of the main body 10 bilaterally to the lateral mons C across the lower abdomen D towards the anterior superior iliac spines E by pressing the adhesive of the rear surface of the main body 10 down firmly.

The features of the invention illustrated and described herein are the preferred embodiments. Therefore, it is understood that the appended claims are intended to cover unforeseeable embodiments with insubstantial differences that are within the spirit of the claims.

What is claimed is:

1. A method of tightening the vaginal opening of a user having a vagina vestibule, a clitoral hood, lateral mons, anterior superior iliac spines and a lower abdomen, the method comprising the steps of:
   providing a gynecological device made from a stretchable material, said gynecological device comprising:
      a main body with a front surface, a rear surface, a first edge, a second edge, a first
   end and a second end; said main body including an adhesive on said rear surface of said main body;
      a plurality of arms having a front surface, a rear surface, a first end and a second end, that extend generally perpendicular from an approximate center of
   said second edge of said main body; said plurality of arms including an adhesive on said rear surface of said plurality of arms,
      wherein a length from said first end to said second end of
   said main body is longer than a length from said first end to said second end of said plurality of arms;
   applying a respective one of said plurality of arms arm to the vagina vestibule bilaterally by pressing said adhesive of said rear surface of each of said respective one of said plurality of arms down firmly;
   pulling said main body upward so that said main body is positioned above said clitoral hood; and
   applying said first end and said second end of said main body bilaterally to the lateral mons across the lower abdomen towards the anterior superior iliac spines by pressing said adhesive of said rear surface of said main body down firmly.

2. The method of claim 1 further comprising the step of:
   providing an applicator tool,
   pressing said applicator tool firmly against said gynecological device to apply said adhesive on said back surface of said main body and said plurality of arms.

3. The method of claim 1 wherein said main body has a generally rectangular shape.

4. The method of claim 1 wherein said plurality of arms have a generally curved first edge and second edge and a uniform width extending from said first edge to said second edge.

5. The method of claim 1 wherein said stretchable material is a high-stretch adhesive support tape.

6. The method of claim 1 wherein said main body has a generally crescent shape.

7. The method of claim 1 wherein said adhesive on said back surface of said main body and said plurality of arms is selected from the group consisting of: medical grade tape, acrylic adhesive, silicone adhesive and hydrocolloid adhesive.

8. The method of claim 1 wherein said plurality of arms are spaced apart on said second edge of said main body.

9. The method of claim 1 wherein said plurality of arms includes a first arm and a second arm.

10. The method of claim 9 wherein:
   a first edge of said first arm is convex and a second edge of said first arm is parallel to said first edge of said first arm,
   a first edge of said second arm is convex and a second edge of said second arm is parallel to said first edge of said second arm, and
   said first arm and said second arm are a mirror image of each other.

\* \* \* \* \*